United States Patent [19]

Speier et al.

[11] Patent Number: 5,836,867
[45] Date of Patent: Nov. 17, 1998

[54] MAGNETIC COUPLING ASSEMBLY FOR ENDOSCOPE

[75] Inventors: Craig J. Speier, Santa Barbara; Arthur James Devine, Escondido, both of Calif.

[73] Assignee: Linvatec Corporation, Largo, Fla.

[21] Appl. No.: 967,516

[22] Filed: Nov. 11, 1997

Related U.S. Application Data

[60] Provisional application No. 60/032,503, Nov. 27, 1996.

[51] Int. Cl.$^6$ .......................................... A61B 1/04
[52] U.S. Cl. .................. 600/112; 354/62; 403/DIG. 1
[58] Field of Search .................................. 600/112, 174, 600/167, 109; 354/62; 359/903, 823, 503, 513; 403/DIG. 1; 335/306; 464/29

[56] References Cited

U.S. PATENT DOCUMENTS

| | | |
|---|---|---|
| 3,062,100 | 11/1962 | Ludewig et al. . |
| 3,900,021 | 8/1975 | Makepeace et al. . |
| 3,917,394 | 11/1975 | Sturdevant . |
| 4,076,018 | 2/1978 | Heckele . |
| 4,115,040 | 9/1978 | Knorr . |
| 4,152,099 | 5/1979 | Bingler . |
| 4,378,952 | 4/1983 | Siegmund . |
| 4,569,333 | 2/1986 | Bel et al. . |
| 4,611,888 | 9/1986 | Prenovitz et al. . |
| 4,685,450 | 8/1987 | Collins et al. . |
| 4,697,894 | 10/1987 | Takamura et al. . |
| 4,740,058 | 4/1988 | Hori et al. . |
| 4,781,448 | 11/1988 | Chatenever et al. . |
| 4,807,594 | 2/1989 | Chatenever et al. . |
| 4,844,071 | 7/1989 | Chen et al. . |
| 4,905,031 | 2/1990 | Mody . |
| 4,969,450 | 11/1990 | Chinnock et al. . |
| 5,014,032 | 5/1991 | Aubert . |
| 5,056,902 | 10/1991 | Chinnock et al. . |
| 5,139,383 | 8/1992 | Polyak et al. . |
| 5,156,141 | 10/1992 | Krebs et al. . |
| 5,204,572 | 4/1993 | Ferreira . |
| 5,359,992 | 11/1994 | Hori et al. . |
| 5,575,757 | 11/1996 | Kennedy et al. . |
| 5,599,278 | 2/1997 | Hibbard . |

FOREIGN PATENT DOCUMENTS

| | | |
|---|---|---|
| 970298 | 9/1958 | Germany . |
| 1 253 407 | 11/1967 | Germany . |
| 57-195339 | 1/1982 | Japan . |
| 1389747 | 4/1988 | U.S.S.R. . |
| 430826 | 6/1935 | United Kingdom . |

Primary Examiner—Beverly M. Flanagan
Attorney, Agent, or Firm—Gene Warzecha

[57] ABSTRACT

An endoscope coupler apparatus and method includes a sealed chamber and a lens assembly movable within the chamber for optically adjusting an image to be received by a video camera. The optical adjustment may be, for example, a focus adjustment or a zoom or orientation adjustment, etc. In a preferred embodiment, spaced permanent drive magnets located in an outer rotatable frame situated outside of the chamber are magnetically coupled with respective permanent driven magnets secured to an inner rotatable frame within the sealed chamber. The outer frame is rotatable but not longitudinally movable about the chamber and rotates the drive magnets and, therefore, the driven magnets. The inner frame is secured to a rotatable cylindrical housing which engages a lens assembly. Rotation of the driven magnets and the cylindrical housing moves the lens assembly longitudinally in response to rotation of an adjustment ring attached to the outer frame.

24 Claims, 6 Drawing Sheets

MAGNETIC COUPLING ASSEMBLY FOR ENDOSCOPE

This application claims the benefit of Provisional application No. 60/032,503, filed Nov. 27, 1996.

BACKGROUND OF THE INVENTION

1. Field of the Invention

The present invention pertains to endoscope couplers for optically and mechanically coupling an endoscope to a video camera. More particularly, the invention relates to endoscope couplers having a lens assembly movable within a permanently sealed chamber by cooperative action with a control mechanism outside the sealed chamber.

2. Description of the Prior Art

Endoscopes have become widely utilized in surgery for viewing body cavities and organs to permit performance of diagnostic and surgical procedures internally without the need for invasive surgical procedures. An endoscope is typically inserted through a small incision or portal providing access to the body cavity. A lens at a distal end of the endoscope is positioned to receive light reflected from a site to be observed, and images of the site can be viewed remotely to conduct diagnostic examinations and to perform closed, or endoscopic surgery. As used herein, the term endoscope refers generically to viewing devices for remotely observing otherwise inaccessible body cavities with minimal trauma and intrusion, including but not limited to arthroscopes, colonoscopes, bronchoscopes, hysteroscopes, cystoscopes, sigmoidoscopes, laparoscopes and ureterscopes, etc.

Endoscopes are sometimes supplied with an eyepiece at the proximal end thereof, and relay lenses in the endoscope typically produce an image for direct viewing through the eyepiece. However, adaptation of video camera technology to endoscopy imaging has enabled the output image of an endoscope to be viewed on a video monitor. Specifically, a video camera is electronically coupled to the video monitor and optically and mechanically coupled with the proximal end of the endoscope. Indirect or video monitor viewing of endoscopic images provides numerous benefits over direct viewing through an eyepiece, including: protection of a direct viewer's vision from high intensity illumination passed through the endoscope and reflecting off bodily tissue; enhancement of operator comfort and freedom of movement; increased endoscope utility and efficiency; reduction in the time required to conduct many endoscopic procedures; simultaneous viewing of endoscopic images by more than one person; and recordation and real time transmission of images of surgical procedures.

An endoscope coupler is required to couple the proximal end of the endoscope to the video camera and may be made as a separate device or in combination with either the endoscope or the video camera. Illustrative endoscope couplers are shown in U.S. Pat. Nos. 4,569,333 (Bel et al.); 4,611,888 (Prenovitz et al.); 4,740,058 (Hori et al.); 4,781,448 (Chatenever et al.); 4,807,594 (Chatenever); 4,844,071 (Chen et al.); 4,969,450 (Chinnock et al.); 5,056,902 (Chinnock et al.) and 5,359,992 (Hori et al.). Endoscope couplers usually include a cylindrical body closed at opposing ends by end windows and containing a lens holder carrying one or more lenses longitudinally movable within the body to optically adjust an image from the endoscope onto a focal plane of the camera. The optical adjustment most commonly used is a focus adjustment and, while it is understood that the invention disclosed herein may be used with other optical adjustments, the description of the invention will be made in terms of a focus adjustment device. Thus, a focusing ring is mounted on the coupler body and is coupled with the interior lens holder to selectively move the lens holder and the lens in response to movement of the focusing ring. Mechanical interconnection between the focusing ring and the lens holder (e.g., by cam pins on the focusing ring riding in slots in the lens holder) permit longitudinal movement of the lens holder in response to focusing ring rotation while preventing rotation of the lens holder.

In order to maintain sterile surgical conditions, endoscope couplers must be sterilized before and after each use. Steam autoclaving has long been the best accepted method of sterilization and is used for all instruments that can withstand the necessary high temperature and pressure. Sterilization of equipment in the autoclave is simple to perform, requires no highly customized equipment or specialized labor and is relatively inexpensive. Instruments that will not survive the steam autoclave process, such as video cameras and prior art endoscopic couplers are treated by less effective or less efficient means such as immersion in sterilization liquid or gas sterilization. However, there is no known conventional endoscopic coupler which can withstand repeated steam sterilization and all known endoscopic couplers are adversely affected when sterilized by submersion in disinfecting solutions or by gas sterilization. For example, the mechanical drive mechanism interconnecting the focusing ring and the lens holder in conventional endoscope couplers allows sterilizing medium to seep into the coupler body around the drive mechanism. Specifically, cam pin and slot drive mechanisms, as well as other mechanical linkages between the focusing ring and the lens holder, provide fluid communication paths between the interior and exterior of the coupler body. Liquid or gas entering the coupler body can create residue on and spot the end windows as well as the interior lens whereby the image presented to the video camera is significantly impaired. Even small amounts of sterilizing liquid or gas in the coupler body can produce serious consequences if deposited on the end windows and/or the lens. Further, minute residual amounts of moisture in the coupler body can produce condensation on the windows and lens during use as heat from illumination directed through the endoscope causes fogging of the relatively cooler windows and lens. Condensation on the windows and lens detracts from image clarity at the video camera and can seriously hamper diagnostic and surgical procedures. Frequently, condensation does not occur until heat from illumination produces a relatively high temperature gradient between the proximal end of the endoscope and the endoscope coupler and, by that time, the surgical procedure is usually well under way. In many cases, the procedure must be temporarily suspended to permit replacement of the endoscope coupler. Moreover, endoscope couplers known to experience problems due to residual moisture must be reconditioned through dismantling, cleaning, drying and reassembling, a process that is time consuming and absorbs scarce personnel resources. Although most conventional endoscope couplers include seals at the cam and slot for preventing leakage of sterilizing fluid into the coupler body, these seals are usually O-ring type seals that perform inadequately under fluid and gas sterilization conditions. Such seals generally fail to prevent entry of fluid or gas into the coupler body and have the further disadvantage of increasing the structural and manufacturing complexity and cost of the endoscope coupler.

It is known in the prior art to provide an endoscope coupler with a sealed chamber containing a lens focused by means of a magnetic field. Specifically, the aforementioned U.S. Pat. No. 5,056,092 (Chinnock et al.) discloses an annular magnet disposed concentrically about the sealed chamber and arranged to move axially in response to rotation of a focusing ring. The interior focusing lens is supported in a magnetically permeable actuator housing defining a closed flux path with the exterior magnet so that the actuator housing and focusing lens are moved axially in response to axial movement of the magnet. This patent also discloses that the actuator housing may be an annular magnet. The resulting coupler structure permits the chamber containing the lens to be effectively sealed since there are no mechanical elements extending into the chamber. However, manufacture of the control arrangement is relatively expensive because each annular magnet must be custom made. Additionally, a ring magnet, once formed, cannot be machined to tailor its fit and orientation in the final assembly. The fit and orientation of the control magnet are crucial in the Chinnock et al. device in order to assure accurate control over the actuation housing position. Accordingly, the magnet must be manufactured to such close tolerances as to practically preclude the use of mass production techniques. Furthermore, while the sealed chamber protects the lens from some of the adverse consequences of sterilization, the Chinnock et al. device utilizes a mechanical cam and helical slot outside the sealed chamber, thus subjecting a significant portion of the mechanical part of the device to being fouled with tissue debris which must be cleaned with difficulty. This design also exposes the mechanical elements to exposure to the harsh, corrosive sterilization environment.

The aforementioned U.S. Pat. No. 5,359,992 (Hori et al.) discloses another endoscopic coupler with magnetic focus control. This device utilizes a plurality of discrete drive magnets circumferentially spaced on the surface of a rotatable focus ring which surrounds a sealed chamber within which a lens assembly is slidably situated. Each of the drive magnets is associated with a respective driven magnet secured on the lens assembly. Rotation of the focus ring causes the drive magnets to follow a helical slot, but since the magnets are also constrained by a longitudinal slot, the resulting motion of the associated driven magnets is longitudinal, thus causing the lens assembly to longitudinally slide within the sealed chamber. The disadvantages associated with this device are comparable to those discussed above with respect to the Chinnock et al. device. In addition, the Hori device does not utilize a closed flux path thus reducing the efficiency of the coupling between the drive magnets and driven mechanism. Furthermore, both the Chinnock et al. and Hori et al. devices establish only a magnetic connection between the drive magnet(s) and the driven mechanism. If either of these devices is dropped or subjected to significant longitudinally directed force, the magnetic connection between the inner and outer structures may be lost, thereby possibly making the coupler inoperative or, at a minimum, necessitating some repair.

A further drawback of conventional endoscope couplers is that the focusing rings commonly do not provide an acceptable tactile response with the result that the focusing rings feel too loose or too tight. Consequently, it is difficult for an operator to gain tactile control during focusing, and lack of proper "feel" detracts from the functional utility of most endoscope couplers. It has been found that minimizing the mechanical portion of the focusing device outside the sealed chamber of a magnetic coupler minimizes friction and enhances the operation of the focusing ring over repeated sterilization cycles.

Accordingly, it is an object of the present invention to overcome the above-mentioned disadvantages of prior art endoscope couplers.

It is another object of this invention to produce an optically adjustable endoscope coupler having a sealed chamber containing a movable lens assembly, the motion of which is driven by a driving mechanism outside the sealed chamber.

It is also an object of this invention to produce an endoscope coupler having a sealed chamber containing a longitudinally adjustable lens assembly wherein the lens assembly is movable without mechanical connections to the outside of the sealed chamber.

Another object of the present invention is to provide a low cost endoscope coupler having a focusing ring for reliably moving a lens assembly axially within the coupler in response to rotation but no axial movement of the focusing ring and without mechanical interconnection of the focusing ring and the lens assembly.

A further object of the present invention is to provide a reliable low cost magnetic drive for positively moving a lens assembly longitudinally within a sealed chamber in an endoscope coupler.

It is also an object of the present invention to provide an endoscope coupler that may be quickly and easily inserted between an endoscope and a video camera or may be formed as an integral part of either the endoscope or the video camera.

It is another object of the present invention to produce an optically adjustable endoscope coupler that can withstand repeated steam sterilization cycles with no significant degradation of performance.

Additionally, it is an object of the present invention to provide an optically adjustable endoscope coupler with a rotatable focusing member having improved tactile response when manually moved by an operator to translate a lens assembly sealed within the coupler.

SUMMARY OF THE INVENTION

These and other objects are accomplished by the preferred embodiment disclosed herein which is an endoscope coupler for mechanically and optically coupling an endoscope to a viewing device. The coupler comprises a lens, a sealed chamber surrounding the lens, the chamber including a peripheral wall disposed about a longitudinal axis and a window permitting light to enter the chamber and the lens. A lens holder is disposed inside the chamber, has a peripheral wall disposed about the longitudinal axis and is movable along the longitudinal axis within the chamber. The lens holder is arranged to cause motion of the lens in the chamber when the lens holder is moved. A hollow cylindrical housing is interposed between the sealed chamber peripheral wall and the lens holder, the cylindrical housing having a proximal end and a distal end and adapted to receive the lens holder. The cylindrical housing comprises driven magnet means supported on the housing and means interconnecting the lens holder and the driven magnet means for transferring motion therebetween. The coupler further comprises drive magnet means supported outside the sealed chamber and magnetically coupled to the driven magnet means through the wall of the chamber. A rotatable focus control member is attached to the drive magnet means for selectively rotating it to thereby rotate the driven magnet means in the sealed chamber in response to rotation of the focus control member about the longitudinal axis of the chamber.

The invention also resides in the method of optically adjusting a coupler adapted for optically coupling an endoscope to a video camera, said method comprising the steps of (a) disposing a lens supported by a cylindrical lens holder in a sealed elongated chamber having an axis, a cylindrical peripheral wall and an axially aligned opening at each end to permit light to pass through said chamber and said lens; (b) providing a hollow cylindrical housing inter-posed between said lens holder and said peripheral wall of said sealed chamber; (c) providing in said sealed chamber, between said cylindrical housing and said lens holder, a motion translating means for translating rotational motion of said cylindrical housing into longitudinal motion of said lens holder; (d) securing a plurality of annularly arranged driven magnets to said cylindrical housing at respective angularly spaced locations about the axis of said chamber; (e) supporting a plurality of annularly arranged drive magnets outside said chamber, each drive magnet being magnetically coupled to a respective driven magnet through the peripheral wall of said chamber; (f) rotating said drive magnets about said axis, while preventing axial movement thereof along said axis, thereby rotating said driven magnets and said cylindrical housing solely as a result of said magnetic coupling and thereby causing said motion translating means to move said lens holder longitudinally.

DESCRIPTION OF THE PREFERRED EMBODIMENT

Figure 1:
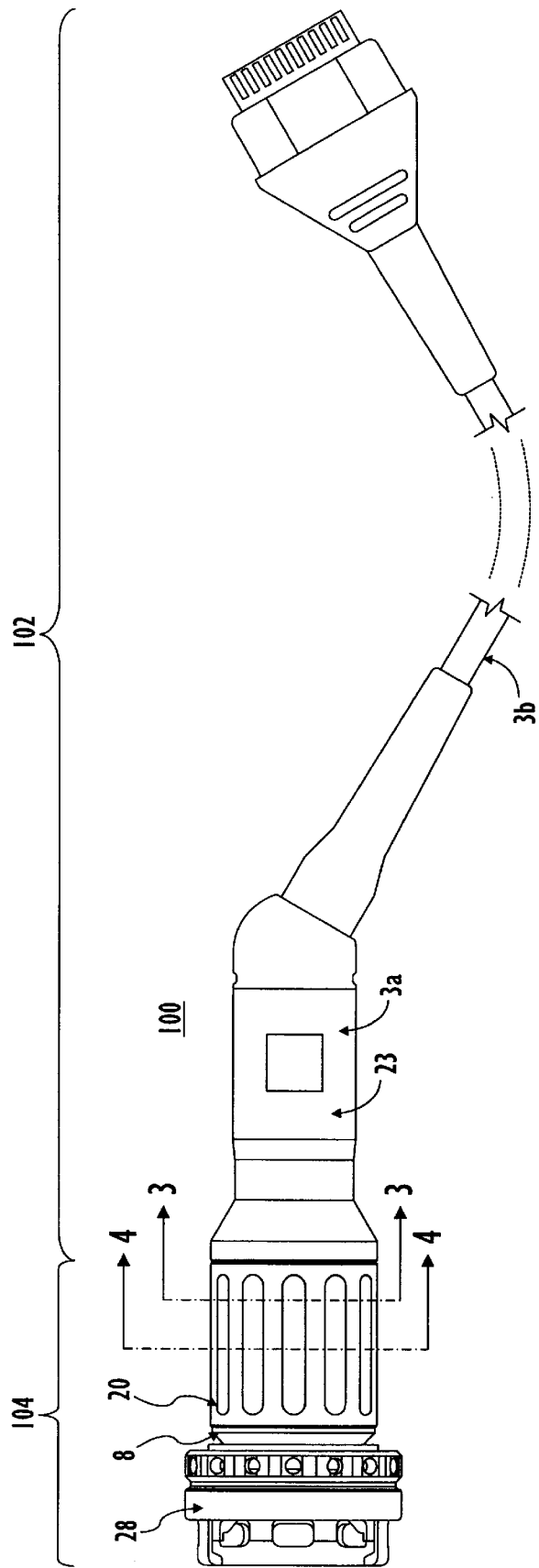
FIG. 1 is a side elevation view of an endoscopic camera/coupler assembly incorporating an endoscope coupler constructed in accordance with the principles of this invention.

As shown in the drawings, endoscopic camera/coupler assembly 100 comprises a video camera portion 102 and an endoscope coupler portion 104. While coupler 104 is shown integrally connected to a video camera, it will be understood that the coupler could be an independent component, which would then need to be attached at one end to an endoscope and at the other end to a camera, or it could be integrally formed with the endoscope and then attachable to a camera. To minimize the time required to cool down after being autoclaved, the external surfaces of camera 100 and coupler 104 are preferably made of a plastic or polymeric material which has poor thermal conductivity and which is electrically non-conductive. Such features of the device are described in a co-pending U.S. patent application Ser. No. 08/606,220, filed Feb. 23, 1996, assigned to the assignee hereof and incorporated by reference herein.

Figure 2:
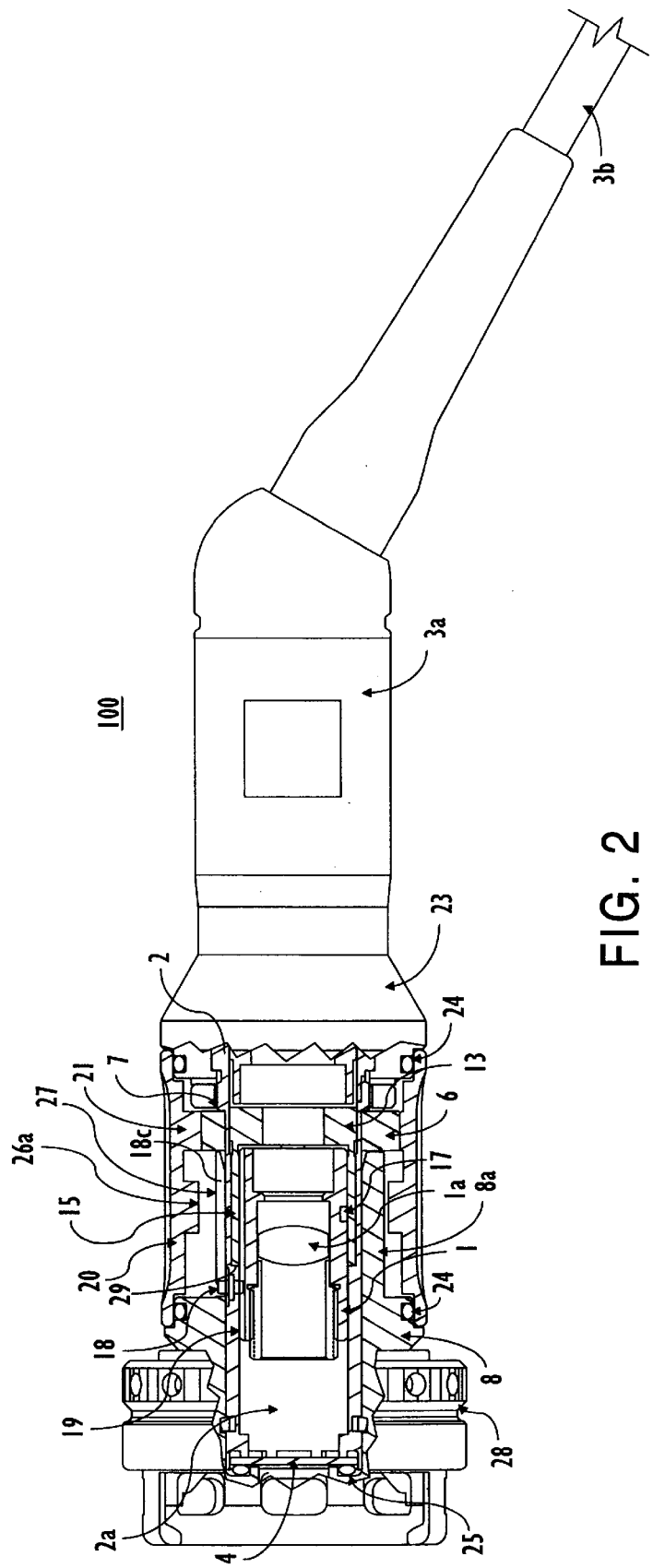
FIG. 2 is a side elevation view of the endoscopic camera/coupler assembly of FIG. 1, partially in cross-section.

As best seen in FIG. 2, the coupler portion 104 comprises a cylindrical lens holder or assembly 1 that slides within a cylindrical body 2 for focusing the image to be received by a video camera in camera portion 102. The lens assembly 1 contains lens 1a which is diagrammatically shown as a single convex lens. It will be understood that different lens arrangements may be used depending on the optical characteristics desired. Body 2 has a window opening at both its proximal and distal ends to enable light from an image to pass through. While the term "opening" may sometimes be used herein instead of "window", it will be understood that body 2 is a sealed chamber and the "opening" enables light transmission without exposing the body interior to ambient. In the preferred embodiment disclosed herein, the proximal end of body 2 houses an integral video camera 3 (e.g. charge coupled device chip) which covers the body opening at one end while the opening at the distal end is sealed by a transparent window 4. To produce a hermetically sealed internal chamber 2a of the body, the window at the distal end is installed with a method such as brazing or soldering while the proximal end of the chamber is sealed by a bulkhead 31 with glass insulated electrical feed through conductors 32. The bulkhead is joined to the body by electron beam welding or any suitable alternate technique which can maintain a hermetic seal. Within the internal sealed chamber 2a is a desiccant 5 designed to hold any small amount of moisture which may be trapped within the chamber during manufacture or which may intrude into the sealed chamber during sterilization. Desiccant 5 prevents the moisture from condensing on the lenses and/or damaging the electronics in the chamber.

Figure 8:
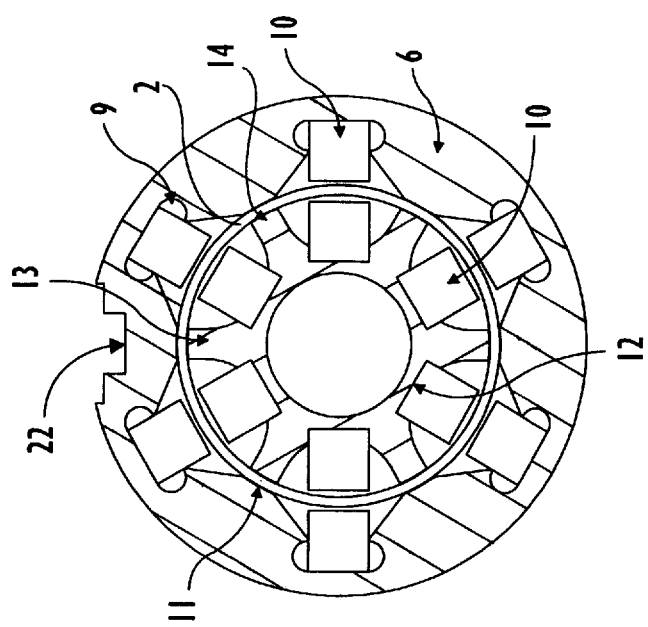
FIG. 8 is a sectional view of FIG. 6 taken along the line 8—8.

On the exterior of body 2 surrounding its peripheral cylindrical wall is a cylindrical drive housing 6 that is adapted to rotate but not translate relative to cylindrical body 2. The translation is prevented proximally by raised shoulder 7 and distally by a cylindrical extension 8a of an exterior interface cap 8 which is situated over the outside of the distal end of body 2. In the preferred embodiment, body 2 is fabricated of titanium or other non-magnetic, biocompatible metal and, drive housing 6 is fabricated of ferromagnetic material. (In the preferred embodiment 416 stainless steel was chosen because it resists corrosion when subjected to sterilization chemicals and processes.) An alternate method to inhibit corrosion would be to plate a more corrosive ferromagnetic material (e.g. steel) with a more chemically inert material (e.g. gold, nickel). Drive housing 6 supports an annular array of circumferentially spaced drive magnets. In the preferred embodiment, drive housing 6 is an annular ring which has a plurality of circumferentially spaced recesses 9, best seen in FIG. 8, each housing a permanent rectilinear magnet 10 which is secured in its respective recess by magnetic attraction to the drive housing. In the preferred embodiment, drive housing 6 has a plurality of narrow radially inwardly extending walls or projections 11 interposed between (and defining) adjacent recesses 9 which, as will be understood below, serve as flux concentrators and bearing surfaces when housing 6 rotates relative to the cylindrical body 2. The radially innermost sides of projections 11 lie on a diameter substantially equal to the outside diameter of body 2.

Similar permanent magnets 10, each with a radially oriented polarity, are secured through magnetic attraction in recesses 12 in a rotatable cylindrical driven housing 13, also fabricated of ferromagnetic stainless steel, situated within sealed chamber 2a. The magnetic attachment of the magnets to their respective annular housings eliminates the need for adhesives which can lose their effectiveness after many sterilization cycles, thus overcoming one of the disadvantages of prior art mechanisms which require adhesives to secure the magnets. The driven housing 13 has a plurality of narrow radially outwardly extending projections 14 and the magnets in driven housing 13 are aligned with and magnetically coupled to the magnets in drive housing 6.

Similarly, the projections 14 on driven housing 13 are aligned with and magnetically coupled to the inwardly extending projections 11 in drive housing 6. The radially outermost sides of projections 14 lie on a diameter substantially equal to the inner diameter of body 2. As a result of the radially directed magnetic coupling, driven housing 13 will rotate in response to a rotation of drive housing 6. The combination of the opposing permanent magnets and the opposing projections forms a closed magnetic flux path for each permanent magnet, thus using the magnetic energy most efficiently. Additionally, because the projections in drive housing 6 and driven housing 13 can be easily custom machined to form bearing surfaces, the radial distance between the projections may be minimized in comparison to the radial distance between the magnets themselves. The inner and outer diameters of the various components are such that projections 11 and 14 are arranged to slide around the inner and outer surfaces of body 2, respectively. While the projections may be in contact with these surfaces, the magnets need not be in contact. In the preferred embodiment, the minimization of this radial distance improves the magnetic coupling strength dramatically. Furthermore, because the projections are relatively narrow, the magnetic flux is concentrated from the relatively wider transverse (facing) surfaces of the magnets. This concentration of magnetic flux results in a more intimate coupling between drive housing 6 and driven housing 13 and significantly reduces hysterysis (i.e. a rotation of drive housing 6 without a corresponding rotation of driven housing 13), thus overcoming another disadvantage of prior art magnetic coupling mechanisms.

Extending distally from driven housing 13 is a hollow cylindrical housing extension 15 having a hole that is adapted to accept a pin 16 which extends radially into the interior of the housing. In the preferred embodiment, extension 15 is integrally formed with driven housing 13. Housing extension 15 is sized to receive lens assembly 1 and pin 16 is adapted to engage a helical groove 17 on the outside surface of lens holder 1. The outside diameter of lens holder 1 is such as to mate with the inner diameter of cylindrical housing extension 15 of driven housing 13. The lengths of housing 15 and lens holder 1 are chosen so as to have the distal side of lens holder 1 extend distally beyond housing 15 when the former is at the proximal-most end of its range of motion. A dual-sided pin 18 is secured in the wall of cylindrical body 2 (by brazing, soldering or welding to maintain the hermetic seal) distally of the distal rim 15a of housing 15 and has a radially inwardly extending pin component 18a adapted to engage a longitudinally extending linear slot 19 on the outer surface of the lens holder 1. The resulting mechanism is a motion translating means which produces, in response to a rotation of drive housing 6, a corresponding rotation of driven housing 13 which puts both a rotational and linear force on the lens holder 1 via pin 16 engaged in helical groove 17. Pin component 18a engaged in the linear slot 19, however, prevents the lens holder 1 from rotating which results in a simple linear translation of the lens holder.

Pin 18 also has a radially outwardly extending pin component 18b which is received in longitudinal keyway slot 18c formed in extension 8a. This enables proper alignment of the components during assembly and prevents relative rotation between body 2 and the interface cap 8.

Optical adjustment of coupler 100 is achieved by moving the drive magnet means to cause a corresponding movement in the driven magnet means and the lens holder. In the preferred embodiment, an outer ring such as focus ring 20 is used to move the drive magnet means. Thus, to focus the image by translating the lens holder, the operator rotates a cylindrical focus ring 20 which has a radially inwardly extending internal tab 21 which engages a groove 22 on the outside cylindrical surface of drive housing 6. Focus ring 20 is limited on its proximal end by the camera housing 23 to prevent translation. In addition, the focus ring has O-rings 24 at its proximal and distal ends in frictional engagement with the camera housing 23 and interface cap 8 to provide the proper tactile response to the operator, as well as to seal the internal components (between focus ring 20 and body 2) from significant intrusion of fluids during sterilization or during use. Interface cap 8 is similarly sealed with an O-ring 25 against the front window to prevent fluid intrusion. In the preferred embodiment the focus ring, interface cap, camera housing and front window are all electrically non-conductive and, with the seals, enable the device to meet the international safety requirement that endoscopic equipment that contacts the patient and/or operator must be electrically isolated from ground or power sources (Medical Equipment Particular Standards for Safety of Endoscopic Equipment of the International Electrotechnical Commission, IEC 601.2.18)

Figure 4:
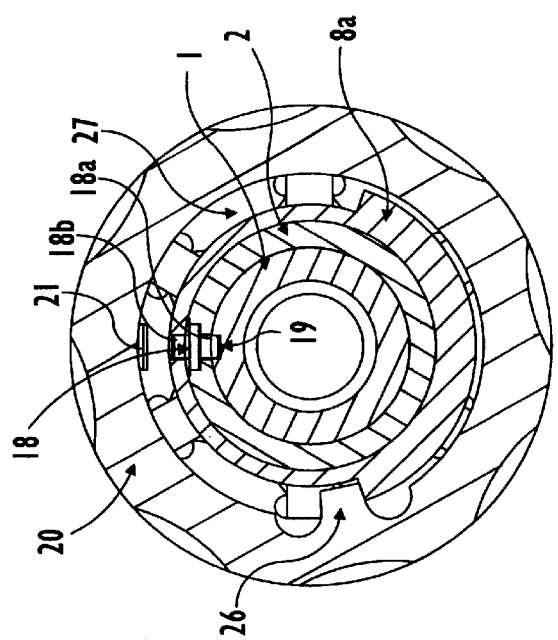
FIG. 4 is a sectional view of FIG. 1 taken along the line 4—4.
Figure 3:
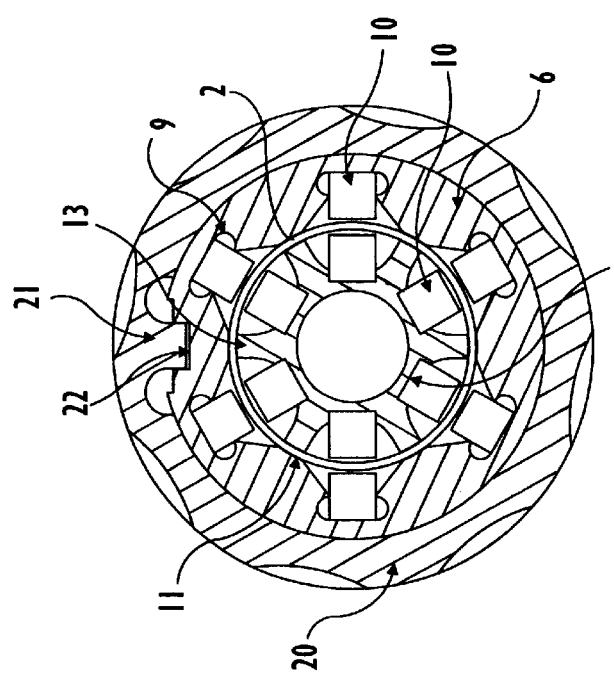
FIG. 3 is a sectional view of FIG. 1 taken along the line 3—3.
Figure 5:
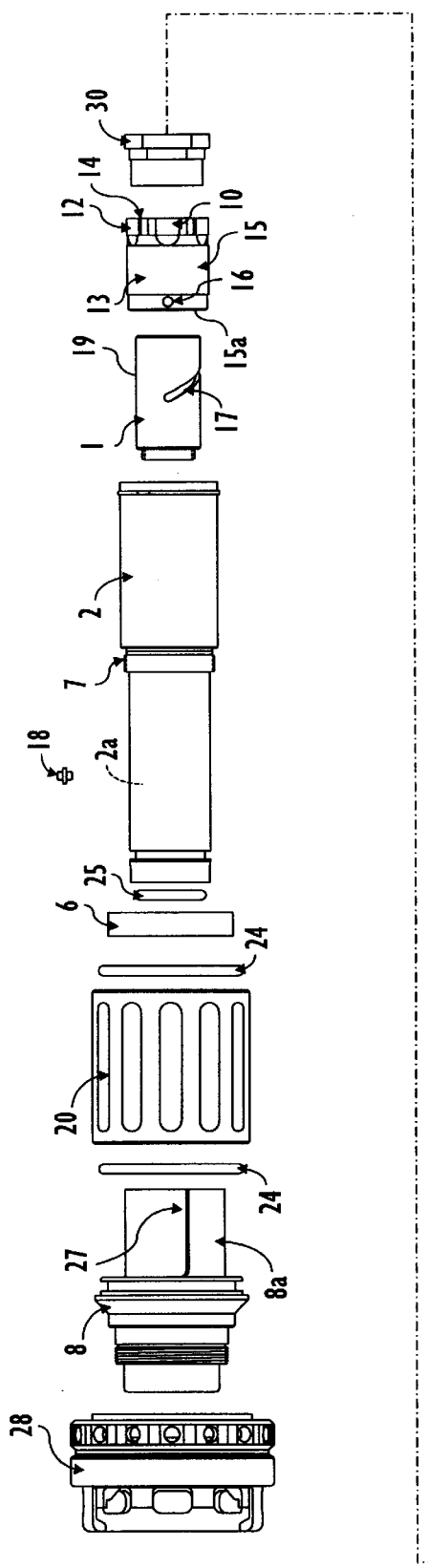
FIG. 5 is an exploded side elevation view of the endoscopic camera/coupler assembly of FIG. 1.
Figure 5:
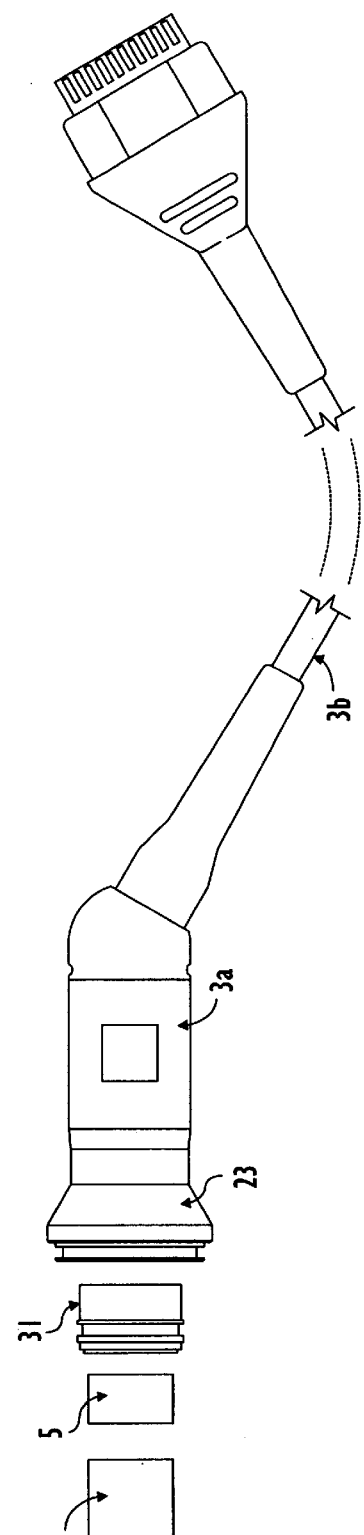
Figure 6:
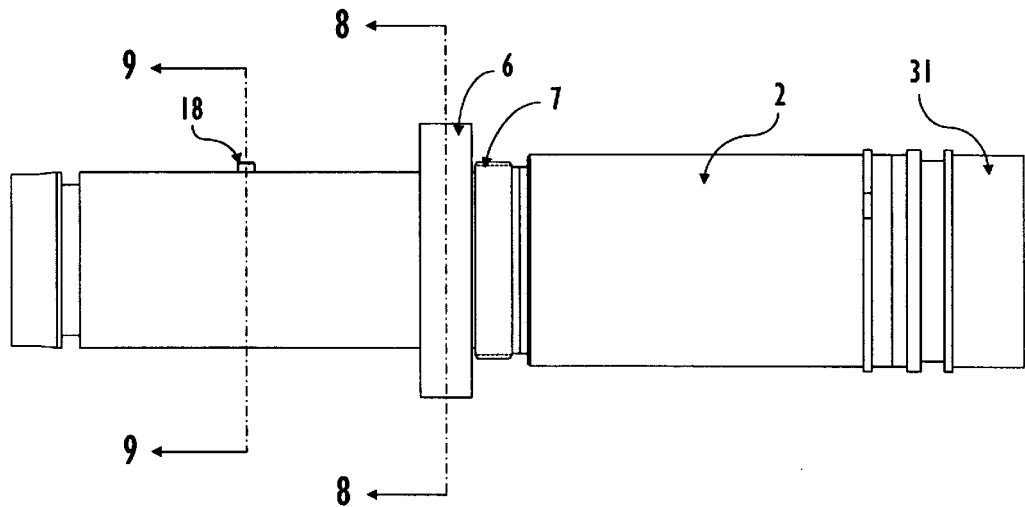
FIG. 6 is an isolated view of a portion of FIG. 5.

The rotation of focus ring 20 is limited by an additional radially inwardly extending tab 26 that is received in a circumferential groove 27 in the external surface of interface cap 8. FIG. 4 shows tab 26 abutting a shoulder at one end of groove 27 while FIG. 2 shows an annular rib 26a from which tab 26 extends inwardly. This control of focus ring travel prevents the operator from damaging the internal mechanism within sealed chamber 2a with the use of excessive force. The interface cap, in turn, houses a mechanism 28 at its distal end to receive an endoscope eyepiece (not shown). The mechanism 28 could also be adapted to receive a cartridge type endoscope with no eyepiece (not shown).

An additional advantage of this camera/coupler 100 compared to the prior art is the simplicity of the focusing mechanism on the exterior of cylindrical body 2. This exterior region is susceptible to the intrusion of sterilization media which can be corrosive and leave residues which can degrade any external mechanism. Some prior art mechanisms have both sliding and rotating parts on the exterior, and as many as four separate tightly toleranced keyways on the cylindrical body. All of these features are subject to degradation after numerous sterilization cycles. The preferred embodiment disclosed herein relies only on a simple rotation of drive housing 6 on the exterior of the cylindrical body 2 which has no slots, grooves or keyways. The linearly and helically moving parts of this mechanism are contained within the hermetically sealed interior chamber 2a of cylindrical body 2, in an environment that is controlled and not subject to degradation during the normal lifetime of this product. There is no mechanical connection between the linearly and rotationally moving parts outside the sealed chamber and the only "connection" between the drive and driven elements is a rotating, non-contiguous connection (which, in the preferred embodiment, is magnetic) through the wall of the sealed chamber.

An additional and important advantage of this camera/coupler 100 is that the lens holder 1 cannot become disengaged from drive housing 6 as in prior art magnetic couplers. Such a disengagement would render the assembly useless, as the operator no longer has control of the lens holder and, therefore, no control of the image. This can seriously hamper diagnostic and surgical procedures. In known prior art magnetic coupler mechanisms, only magnetic force prevents disengagement of the lens holder. The magnetic force is limited and can easily be overcome by a force produced when the coupler is dropped, a not uncommon occurrence. In the preferred embodiment, lens holder 1 is longitudinally retained mechanically by engagement of pin 16 in driven housing 13 with slot 17 in the lens holder. Housing 13 is, in turn, retained distally by a shoulder 29 in cylindrical body 2, and retained proximally by a cylindrical spacer 30. Therefore, lens holder 1 is secured both mechanically and magnetically.

Figure 7:
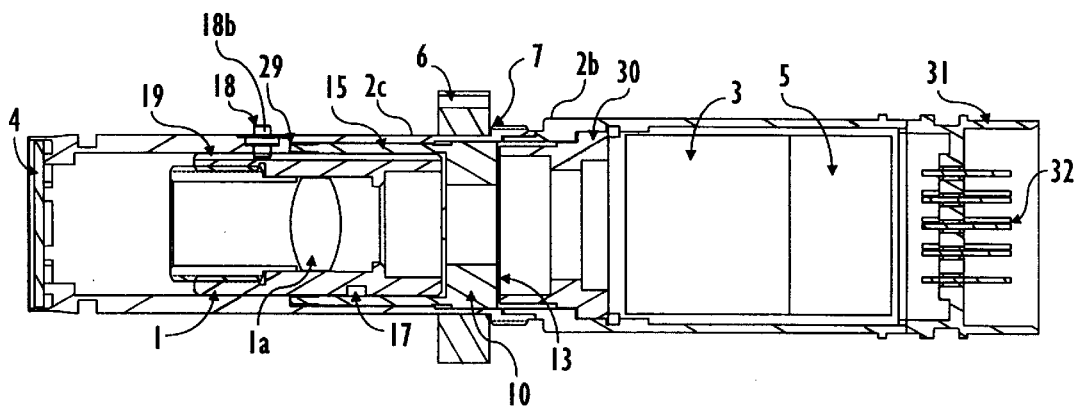
FIG. 7 is a cross-sectional view of FIG. 6.
Figure 9:
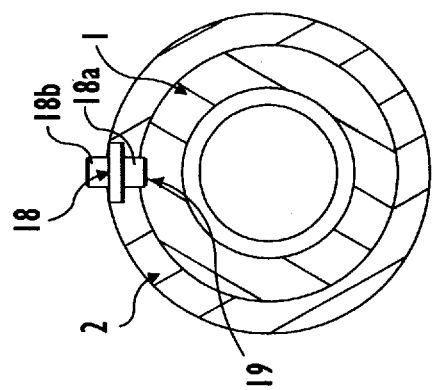
FIG. 9 is a sectional view of FIG. 6 taken along the line 9—9.

As shown in FIG. 7, body 2 can have a proximal section 2b welded or otherwise hermetically attached to a distal section 2c as an alternative embodiment. Such a structure would not affect the operation of the invention.

It will be understood that, rather than being integrated into the camera, the coupler may be integrated into the endoscope. Additionally, the coupler may be a separable unit having some conventional attachment means (threads, etc.) by which it could be joined to an independent camera assembly and to an independent endoscope. Additionally, the principles disclosed herein may be adapted to other than focusing mechanisms. For example, the optical coupling structure used in the preferred embodiment for focusing could be used for zooming (changing the magnification of the image on the video camera) or it could also be used to rotate an unsymmetrical, internal optical part (e.g. a dove prism) to change the orientation of the image on the video camera.

Camera 100 can be provided with a user activatable button (not shown) incorporating a Hall effect sensor in order to remotely operate a peripheral device such as a tape recorder, etc. The sensor could be on a printed circuit board (not shown) near camera 3 and could be activated through the wall of body 2 by a magnet-retaining button on the exterior of the body and movable relative to the sensor.

While the preferred embodiment disclosed herein utilizes a rotatable adjustment control ring, it will be understood that, with appropriate modifications, the device can be produced with a longitudinally slidable adjustment control member. This, in turn, would activate a slidable internal driven magnet means which, with a suitable motion translating mechanism, could rotate or slide a lens assembly.

It will be understood by those skilled in the art that numerous improvements and modifications may be made to the preferred embodiment of the invention disclosed herein without departing from the spirit and scope thereof.

What is claimed is:

1. An adjustable endoscope coupler for optically coupling an endoscope to a viewing device, said coupler comprising:
    a lens;
    an elongated sealed chamber surrounding said lend and having a longitudinal axis, said chamber comprising a first peripheral wall and having an axially aligned opening at each end for permitting light to pass through said chamber and said lens;
    a lens holder supporting said lens and movable along said longitudinal axis within said chamber, said lens holder comprising a second peripheral wall parallel to said first peripheral wall;
    a hollow housing comprising a third peripheral wall interposed between said first and second peripheral walls, said housing having an open proximal end, an open distal end and adapted to slidable receive said lens holder therein;
    drive means movably supported outside said sealed chamber;
    driven means for moving said housing in response to motion of said drive means;
    motion transmitting means interconnecting said lens holder and said housing for transferring motion therebetween;
    wherein said drive means acts through said first peripheral wall to move said driven means.

2. An adjustable endoscope coupler according to claim 1 wherein said driven means comprises a driven magnet means having at least one first magnet and wherein said drive means comprises a drive magnet means having at least one second magnet magnetically coupled to said at least one first magnet.

3. An adjustable endoscope coupler according to claim 2 wherein said drive magnet means further comprises:
    a movable adjustment control member attached to said drive magnet means for selectively moving said drive magnet means to thereby move said driven magnet means in said sealed chamber in response to movement of said adjustment control member relative to said sealed chamber.

4. An adjustable endoscope coupler according to claim 2 wherein said drive magnet means further comprises:
    means for enabling rotation of said drive magnet means relative to said sealed chamber while limiting translation relative thereto.

5. An adjustable endoscope coupler according to claim 2 wherein said drive magnet means and said driven magnet means each comprise an annular array of a plurality of first and second magnets, respectively.

6. An endoscope coupler according to claim 5 wherein said drive magnet means and said driven magnet means each comprise a cylindrical annular housing formed of ferromagnetic material and retaining said first and second magnets thereto, respectively.

7. An endoscope coupler according to claim 6 wherein said drive magnet means further comprises an annular ring having a plurality of radially inwardly facing recesses for receiving a like plurality of magnets, said recesses separated by radially inwardly extending, flux concentrating projections and said driven magnet means further comprises an annular ring having a plurality of outwardly facing recesses for receiving a like plurality of magnets, said recesses separated by radially outwardly extending, flux concentrating projections.

8. An adjustable endoscope coupler according to claim 7 wherein said projections are in sliding contact with the respective surfaces of said sealed chamber.

9. An adjustable endoscope coupler according to claim 7 wherein said projections also extend longitudinally a predeterined distance.

10. An adjustable endoscope coupler according to claim 1 wherein said driven means is supported adjacent said proximal end of said hollow housing.

11. An adjustable endoscope coupler according to claim 1 wherein said drive and driven means each comprise a plurality of annularly arranged magnets, each of which is a rectilinear solid and is situated in radial alignment with the axis of said elongated sealed chamber.

12. An adjustable endoscope coupler according to claim 1 wherein said motion transmitting means interconnecting said lens holder and said driven means comprises a slidable mechanical connection means comprising a pin on one of said lens holder and said driven means and a cooperating slot on the other.

13. An adjustable endoscope coupler according to claim 1 wherein said motion transmitting means interconnecting said lens holder and said driven means comprises a slidable mechanical connection means comprising a pin on said housing engaging a helical slot on said lens holder and a pin on said sealed chamber engaging a linear slot on said lens holder.

14. An adjustable endoscope coupler comprising:
   a sealed chamber having a cylindrical peripheral wall, an axis and light transparent ends;
   a lens assembly comprising a lens and a cylindrical lens holder axially aligned within said sealed chamber;
   a rotatable cylinder interposed between said lens assembly and said cylindrical peripheral wall;
   mechanical motion translating means interposed between said lens assembly and said rotatable cylinder for converting rotational motion of one component to linear motion of the other component;
   driven means attached to said rotatable cylinder for rotating same in response to a stimulus from outside said sealed chamber; and
   drive means situated outside said sealed chamber for rotating said driven means.

15. An endoscope coupler according to claim 14 wherein said motion translating means further comprises:
   first motion limiting means for preventing linear motion of said lens assembly without rotation of said rotatable cylinder; and
   second motion limiting means for preventing rotational motion of said lens assembly relative to said axis.

16. The method of optically adjusting a coupler adapted for optically coupling an endoscope to a video camera, said method comprising the steps of:
   (a) providing a lens supported by a cylindrical lens holder in a sealed elongated chamber having an axis, a cylindrical peripheral wall and an axially aligned opening at each end to permit light to pass through said chamber and said lens;
   (b) interposing a hollow cylindrical housing between said lens holder and said peripheral wall of said sealed chamber;
   (c) providing in said sealed chamber, between said cylindrical housing and said lens holder, a motion translating means for translating rotational motion of said cylindrical housing into longitudinal motion of said lens holder;
   (d) securing a plurality of annularly arranged driven magnets to said cylindrical housing at respective angularly spaced locations about the axis of said chamber;
   (e) supporting a plurality of annularly arranged drive magnets outside said chamber, each drive magnet being magnetically coupled to a respective driven magnet through the peripheral wall of said chamber; and
   (f) rotating said drive magnets about said axis while preventing axial movement thereof along said axis, thereby rotating said driven magnets and said cylindrical housing as a result of said magnetic coupling and thereby causing said motion translating means to move said lens holder.

17. A method according to claim 16 wherein said step of rotating said drive magnets further comprises the steps of:
   providing a cylindrical control member axially aligned about said sealed chamber and joined to all of said drive magnets; and
   rotating said cylindrical control member about its axis.

18. A method according to claim 16 further comprising the step of preventing longitudinal motion of said plurality of drive magnets, said plurality of driven magnets and said cylindrical housing relative to said sealed chamber.

19. A method according to claim 17 further comprising the step of providing an outer magnetically conductive housing to retain said drive magnets, said outer housing having a radially inwardly extending projection between adjacent drive magnets, and providing an inner magnetically conductive housing to retain said driven magnets, said inner housing having a radially outwardly extending projection between adjacent driven magnets, each of said projections lying in a radial plane.

20. A method according to claim 19 further comprising the step of extending each of said projections longitudinally a predetermined distance.

21. A method according to claim 16 further comprising the step of retaining said drive magnets and driven magnets within respective cylindrical housings solely by magnetic attraction therebetween.

22. The method of optically adjusting a coupler adapted for optically coupling an endoscope to a video camera, said method comprising the steps of:
   providing a sealed cylindrical chamber;
   providing within said sealed chamber a slidable lens assembly;
   providing within said sealed chamber a mechanical motion translating means for moving said lens assembly;
   providing a drive means adjacent the exterior of said sealed chamber for non-contiguously causing motion of said driven means within said sealed chamber;
   providing a driven means attached to said motion translating means for being non-contiguously moved by said drive means; and
   moving said drive means relative to said sealed chamber to thereby move said lens assembly.

23. A method according to claim 22 wherein said drive means and said driven means are magnetically coupled.

24. A method according to claim 22 further comprising the step of rotating and not translating said drive means in order to rotate and not translate said driven means.

* * * * *